United States Patent [19]

Luomaranta

[11] 4,290,499

[45] Sep. 22, 1981

[54] APPARATUS FOR TESTING AND FITTING CROSS-COUNTRY SKIS

[75] Inventor: Mauri Luomaranta, Sault Ste. Marie, Canada

[73] Assignee: Scandinavian Ski Shop Limited, Sault Ste. Marie, Canada

[21] Appl. No.: 144,307

[22] Filed: Apr. 28, 1980

[30] Foreign Application Priority Data

Mar. 12, 1980 [CA] Canada .................................... 347499

[51] Int. Cl.³ ........................ G01G 23/36; G01G 3/14
[52] U.S. Cl. .................................. 177/48; 177/210 R
[58] Field of Search ................... 177/45, 47, 48, 177, 177/210 R, 209; 73/849

[56] References Cited

U.S. PATENT DOCUMENTS

| 2,095,268 | 10/1937 | Roberts | 177/209 X |
| 2,313,156 | 3/1943 | Kratt, Jr. | 177/209 X |
| 3,305,036 | 2/1967 | Walters | 177/209 |
| 3,964,300 | 6/1976 | Howe | 73/849 |
| 4,195,532 | 4/1980 | Pauls | 73/849 |

FOREIGN PATENT DOCUMENTS 1015977 8/1977 Canada .

Primary Examiner—George H. Miller, Jr.
Attorney, Agent, or Firm—Stevens, Davis, Miller & Mosher

[57] ABSTRACT

Apparatus is disclosed for the testing and fitting of cross-country skis including means to support the cross-country ski having sensor means distributed along its length and width adapted to emit a signal when the bottom surface of the cross-country ski presses them, display means adapted to indicate the origin of the signals from the sensor means and adjustable loading means to exert predetermined forces to points along the top surface of the ski and load measuring means adapted to indicate the applied load.

10 Claims, 3 Drawing Figures

APPARATUS FOR TESTING AND FITTING CROSS-COUNTRY SKIS

This invention relates to an apparatus for testing and fitting cross-country skis.

It is known that a warped ski will not track in a straight line if one of the edges, inner or outer, at the tip or at the tail, is bearing more weight than the edge immediately opposite on the other side of the ski. This condition tends to make the ski steer to one side or the other away from a straight line, making skiing difficult and causing increased wear to the running surface wax and, perhaps even to the running surface itself. A cross-country ski should be constructed in such a way that the running surface or underside of the ski remains horizontally flat without torsional irregularities under widely varying degrees of vertical camber flexing. Such flatness is necessary because a properly constructed cross-country ski must exhibit two properties in order to function correctly, the first being grip when a ski is fully weighted and momentarily stationary and the other is glide when the ski is only partially weighted and moving over a snow surface. Although these properties of a cross-country ski are also directly connected with correct waxing and weight distribution, the condition of flatness contributes to the performance of these functions. Therefore, it is important to evaluate a ski for flatness under both unstressed and stressed conditions.

It is also important that the weight of the skier be equally distributed along the entire running weight of a cross-country ski, whether the ski be fully weighted or in a condition of partial weighting. This may be accomplished by testing to find the point on the top face of the ski where force may be applied to result in substantially equal distribution of loading over the portions of the surface of the ski which would contact the snow surface. Of course, with varying degrees of weighting, there will be corresponding varying areas of running surface of the ski in contact with the snow surface. It is considered desirable that the running surface increase in proportion to the amount of downward weighting applied to the top surface so that the pressure along the bottom of the ski does not increase appreciably despite increased loading. Overall ski camber and stiffness influence this performance characteristic and it is therefore important to know the strength of the ski in order to match it to a particular skier. It is also important to know the particular point on the top face of the ski at which the weight of the skier should be applied to result in even distribution across the entire ski running surface.

It has been observed than an average skier of relatively low athletic ability usually exerts the majority of his weight on the heel of his foot. Therefore, a ski binding may be placed on the ski so as to position the ball of his foot at a desired location. It has been observed that more athletic skiers or ski racers tend to exert more pressure on the ball of the foot, therefore, the binding may be again placed appropriately in relation to the predetermined point.

It is an object of this invention to provide an apparatus which will provide a relatively simple, accurate and effective means of fitting cross-country skis to the body weight and athletic ability of purchasers thereof.

It is an object of this invention to provide an apparatus for testing cross-country skis for longitudinal warp both under conditions of stress and lack of stress.

It is an object of this invention to provide an apparatus for testing the running surface of cross-country skis for straightness under varying degrees of stress.

It is an object of this invention to provide an apparatus for ascertaining the longitudinal flex pattern of a cross-country ski from the tip to the tail toward the center point of maximum ski strength simultaneously.

It is an object of this invention to provide an apparatus for ascertaining the total camber strength of any ski when it is fully flattened under stress.

It is an object of this invention to provide an apparatus for determining the center of maximum strength and equilateral ski loading fore and aft from which may be deduced the correct position for placement of the ski binding.

The apparatus of this invention comprises a flat bed adapted to support a cross-country ski, sensor means distributed at pre-determined points along the length and width of said flat bed, each of said sensor means being adapted to emit a signal in response to force exerted on it by the running surface of a cross-country ski supported on said flat bed, display means adapted to indicate the origin of the signals emitted from each of said sensor means, adjustable loading means adapted to exert pre-determined forces to points along the top surface of said ski and load measuring means adapted to indicate the amount of the applied load.

It will be appreciated that this apparatus may be constructed in a variety of embodiments. The principle of the apparatus is a provision of means to identify points on the lower surface of a ski which are supporting the weight of the ski and the force exerted upon it at selected points. By observation of such data with a number of different weighting forces applied at various points, one is able to determine the physical characteristics of the ski such as the flatness of the ski and the strength of the vertical camber flex. Moreover, one may determine the point at which the binding should be located, to give best distribution of applied loading over the running surface of the ski.

In the embodiments presently envisaged, the weighting means may be moveable back and forth over a central portion of the length of the flat bed, thereby permitting it to be located over a number of points along the central portion of a ski on said flat bed or it may be fixed near a central portion of the flat bed and applied to various points on a ski by simply moving the ski along the length of the flat bed.

The loading means might assume a variety of forms ranging from a simple loading with weights or loading by means of a screw, lever or motor driven press or other conventional means. The load measuring means may be incorporated into the loading means itself to measure the applied load or may be located in the support for the flat bed to measure the load transmitted to the flat bed. In either case, conventional means such as scales and meters may be used to indicate the applied load.

The sensor means of this invention may be any of a number of conventional means which will signal the presence of a force applied to it. The range of such devices that are useful in the construction of this invention include those that would emit a signal proportional to the amount of force exerted on it, those that would emit a signal proportional to the amount of force exerted on it within threshold limits and those that would emit a fixed signal after a certain threshold was exceeded.

The display means of this invention could also include any of a number of conventional display systems. A simple type of display which would be suitable for sensor means of the type that emits a fixed signal after a predetermined threshold is exceeded might consist of a light for each sensor which would switch on in response to emission of a signal. The lights would be positioned relative to one another to indicate to the observer which sensors were activated at any particular time. For example, the sensors may be distributed in pairs along the length of the flat bed, each pair having sensors opposite one another on either side of the longitudinal axis of the flat bed. A single pair of sensors may be located near the lateral axis of the flat bed with successive opposite equidistantly spaced pairs on either side of said single pair of sensors. The sensors may be located beneath feeler plates and may comprise electrical microswitches which are activated by the application of predetermined pressure to the feeler plates. Each light in the panel of lights may be connected to a microswitch and adapted to be switched on when said microswitch is activated. The panel of lights would be arranged to correspond to the arrangement of microswitches so as to indicate which microswitches have been activated.

Similarly, mechanical means such as toggle switches or the like might be activated by the signal instead of a light. It is conceivable that audio means could also be used for this purpose.

More sophisticated display means might be used where the sensor emits a signal proportional to the force applied to it. Such display means might not only indicate the application of a force at a particular point along the ski but also the size of that force. Again, many conventional systems could be used ranging from simple meters for each sensor to a display screen showing the ski schematically where sensor signals would generate colors of variable intensity or hue over the depicted ski to indicate the size of the forces exerted thereon.

In the figures.

Figure 1:
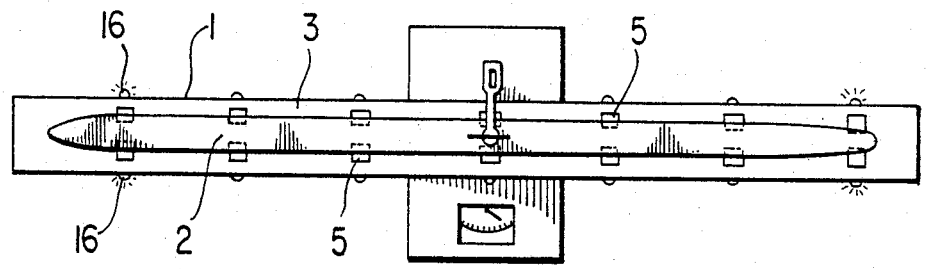
FIG. 1 is a plan view of a preferred embodiment of this invention.
Figure 2:
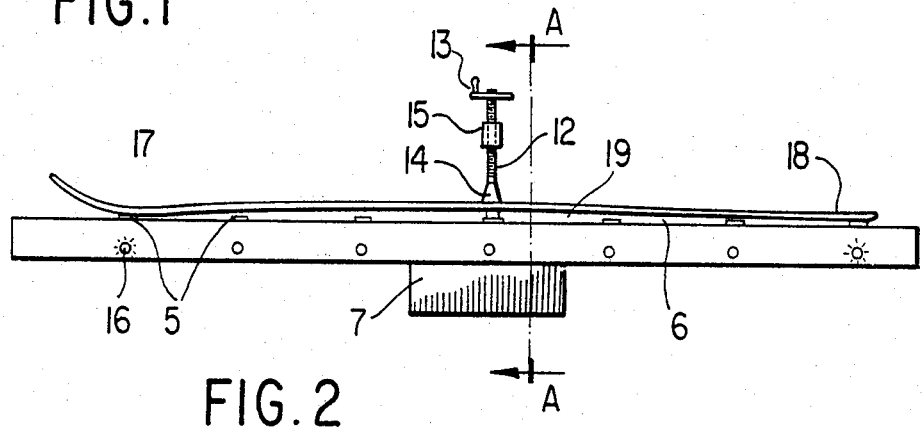
FIG. 2 is a front view of that embodiment.
Figure 3:
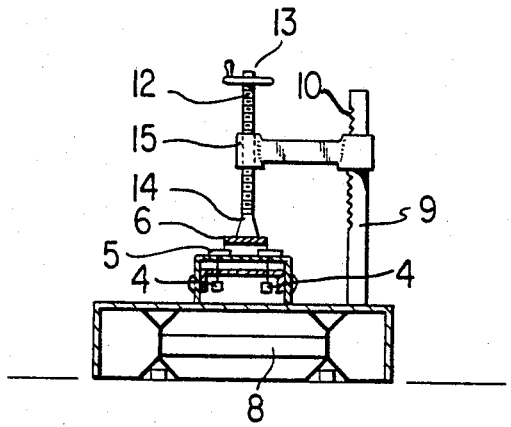
FIG. 3 is an end view of said embodiment.

As shown in the figures, the flat bed (1) comprises a rigid inverted aluminum U channel on which a ski (2) may be placed in the upright position, the longitudinal axis of the ski coinciding with the longitudinal axis of the aluminum channel. It has been found convenient to use an aluminum channel of approximately 2 meters in length. Along the top surface (3) of the aluminum channel at predetermined and regular intervals are mounted a series of 14 sensors (4) being microswitches calibrated to uniform pressure sensitivity. These sensors are located under loosely fitting feeler plates (5) on the top surface of the aluminum channel and placed so as to coincide with the running surface (6) of a ski placed in the upright position along the longitudinal axis of said aluminum channel. At the center of and under the aluminum channel, is an integrated assembly (7) incorporating a weigh scale (8) and an upright metal bar (9) in which tooth like serrations (10) have been cut. The metal bar (9) is placed in an offset position to one side of the aluminum channel. A screw-press (12) having a handle (13) and a gimbal mounted foot (14) is threaded through a cast metal die (15) which is slideable vertically along the metal bar (9) when tilted forward and which locks into the serrations (10) when tilted upright.

An electrical power transformer (not shown) is incorporated into the aluminum channel to reduce conventional electrical voltage to one appropriate to power small lights (16) mounted on the aluminum channel bed, positioned in such a way as to coincide with the positions of each of the micro-switches mounted on the top face of the aluminum channel. These lights are operated by means of relays (not shown) which form an integral part of each micro switch. When a predetermined pressure is applied to a feeler-plate of a switch, it triggers electrical current to activate a light corresponding to that micro-switch. Thus, each micro-switch/light combination acts as a display means.

In operation, a ski is placed on the aluminum channel over the feeler plates of the sensors. A check may be made to determine whether the ski lays flat in the no load position by observing whether the lights are lit on either side of the longitudinal axis of the aluminum channel at the points of contact (17) and (18).

The cast metal die (15) of the screw press assembly is then tilted forward to quick release, lowered to rest the foot (14) on the longitudinal center axis of the ski near the center of gravity of the ski and tilted back to lock into the serrations (10). The handle (13) is then gripped by an operator and then turned to lower the screw press (12) until sufficient force is exerted to flex the camber (19) of the ski enough to light up additional lights. Simultaneously, the load measuring weigh scale (8) of the assembly (7) shows the force being exerted by the press (12) at any particular moment. As other lights are activated the operator may record the force of the press. The operator may also assess the flatness of the running surface of the ski by observing whether lights on either side of its longitudinal axis are activated together as the ski is pressed lower and lower.

It has been found that if cross-country skis are classified into the following major categories that the strength of the vertical camber flex of each ski should be selected in accordance with the data in the following table.

(a) elderly beginners and beginners without apparent athletic ability, (b) athletic beginners and skiers with two or more years of cross-country skiing experience, (c) citizen racer or a skier who regularly participates in cross-country ski loppets or fun races, along with those skiers having four or more years experience, (d) top racers.

| Weight of Skier | Categories | | | |
|---|---|---|---|---|
| (lbs.) | (a)* | (b)* | (c)* | (d)* |
| 80 | 30–40 | 40–50 | | |
| 90 | 35–45 | 45–55 | | |
| 100 | 40–50 | 50–60 | 60–70 | 70–80 |
| 110 | 45–55 | 55–65 | 65–75 | 80–90 |
| 120 | 50–60 | 60–70 | 70–80 | 90–100 |
| 130 | 55–65 | 65–75 | 75–85 | 100–110 |
| 140 | 60–70 | 70–80 | 80–90 | 110–120 |
| 150 | 65–75 | 75–85 | 85–95 | 120–130 |
| 160 | 70–80 | 80–90 | 90–100 | 130–140 |
| 170 | 75–85 | 85–95 | 95–105 | 140–150 |
| 180 | 80–90 | 90–100 | 100–110 | 150–160 |
| 190 | 85–95 | 95–105 | 105–115 | 160–170 |
| 200 | 90–100 | 100–110 | 110–120 | 170–180 |
| 210 | 95–105 | 105–115 | 115–125 | 180–190 |
| 220 | 100–110 | 110–120 | 120–130 | 190–200 |

*The downward screw press force in lbs. exerted on one ski (25) to obtain simultaneous activation of the 4 lights on either side of the centre lights (26). Centre lights (26) will activate at the weight of the skier or less.

Therefore, an operator knowing the weight and classification of a skier is able to test any particular skis to determine whether they have the correct camber strength for optimum performance.

Further, by observing the order in which the lights are successively activated on the display panel and by changing the point at which load is applied to the ski, the operator may determine the point at which load may be applied to the ski to obtain even distribution of the load over the length of the ski.

It is known that skiers of the (a) class above exert most of their weight through the ball of the foot while racers in the (d) class would exert most of their weight in the area of the largest and second largest toes. Accordingly, by knowing the classification of the particular skier and the dimensions of his foot, an operator is able, having determined the point of even load distribution, to locate the optimum position for the placement of the bindings.

The simplicity of operation of this invention will allow sales personnel, without special knowledge or experience, to quickly and easily select skis of the correct flexing characteristics, camber and overall strength for any prospective customer.

In another simpler embodiment of the apparatus of the invention there are only 7 sensors located along the longitudinal axis of the center line. Feeler plates extend over each sensor across the width of a ski. In the embodiment the testing of the camber flex and location of the binding is carried out as before but the apparatus does not test the flatness of the ski under various loading conditions. Initial flatness may be tested by laying the ski on the flat bed and simply observing whether it lies flat.

It will be apparent to those skilled in the art that the principle of this invention may be put in operation by means of a number of apparatus similar in construction to that described above. It will be understood, therefore, that the description herein is illustrative only and is not to be construed as limiting of the invention which is claimed in the following claims.

The embodiments of the invention in which an exclusive property or privilege is claimed are defined as follows:

1. A flat bed adapted to support a cross-country ski, sensor means distributed at pre-determined points along the length and width of said flat bed, each of said sensor means being adapted to emit a signal in response to force exerted on it by the running surface of a cross-country ski supported on said flat bed, display means adapted to indicate the origin of the signals emitted from each of said sensor means, adjustable loading means adapted to exert pre-determined forces to points along the top surface of said ski and load measuring means adapted to indicate the amount of the applied load.

2. The apparatus of claim 1 where the sensors are distributed in pairs along the length of the flat bed, each pair having sensors opposite one another on either side of the longitudinal axis of the flat bed.

3. The apparatus of claim 2 in which there is a single pair of sensors near the lateral axis of the flat bed with successive opposite equidistantly spaced pairs on either side of said single pair of sensors.

4. The apparatus of claim 3 where the sensors are located beneath feeler plates.

5. The apparatus of claim 4 where the sensors are electrical microswitches which are activated by application of predetermined pressure to the feeler plates.

6. The apparatus of claim 5 where the display means comprises a panel of lights, each of which is connected to a microswitch and adapted to be switched on when said microswitch is activated, said panel of lights being arranged to correspond to the arrangement of the microswitches so as to indicate which microswitches have been activated.

7. The apparatus of claim 6 in which the adjustable loading means comprises a screw press threaded through a die which is slideable vertically along an upright serrated bar when tilted and lockable to said serrated bar when righted, said upright bar being mounted adjacent the lateral central axis of said flat bed, said loading means being adapted to locate said screw press over the longitudinal axis of said flat plate.

8. The apparatus of claim 1 in which the sensors are distributed along the longitudinal axis of the flat bed with a single sensor near the lateral axis of the flat bed and successive opposite equidistantly spaced sensors on either side of said single sensor.

9. The apparatus of claim 8 in which the sensors are microswitches located beneath feeler plates on the flat bed, said microswitches being adapted to activate a display panel of corresponding lights, wherein each light is turned on when its respective microswitch is activated.

10. The apparatus of claim 9 in which the adjustable loading means comprises a screw press threaded through a die which is slideable vertically along an upright serrated bar when tilted and lockable to said serrated bar when righted, said upright bar being mounted adjacent the lateral central axis of said flat bed, said loading means being adapted to locate said screw press over the longitudinal axis of said flat plate.

* * * * *